United States Patent [19]

Schmidt et al.

[11] Patent Number: 4,661,605

[45] Date of Patent: Apr. 28, 1987

[54] 3-(ETHER AND THIOETHER)-3-(INDOLYL)-PHTHALIDES

[75] Inventors: Paul J. Schmidt, Sharonville; William M. Hung, Cincinnati, both of Ohio

[73] Assignee: The Hilton-Davis Chemical Co., Cincinnati, Ohio

[21] Appl. No.: 694,568

[22] Filed: Jan. 24, 1985

Related U.S. Application Data

[62] Division of Ser. No. 338,008, Jan. 8, 1982, Pat. No. 4,535,172.

[51] Int. Cl.$^4$ ............................................ C07D 405/04
[52] U.S. Cl. ................................................... 548/463
[58] Field of Search ........................................ 548/463

[56] References Cited

U.S. PATENT DOCUMENTS 3,941,807  3/1976  Borrov .............................. 548/463
4,431,819  2/1984  Schmidt et al. .................... 548/463

OTHER PUBLICATIONS

M. Newman and C. McCleary, J. Amer. Chem. Soc. 63, 1537–1541 (1941).
M. Newman and C. Courduvelis, J. Org. Chem. 30, 1795–1800 (1965).
M. Newman and C. Courduvelis, J. Amer. Chem. Soc. 88, 781–784 (1966).
M. Newman and L. Lala, Tetrahedron Letters 34, 3267–3269 (1969).
M. Bhatt and K. Kamath, J. Chem. Soc. (B), 1036–1044 (1968).

*Primary Examiner*—Robert W. Ramsuer
*Attorney, Agent, or Firm*—Terrence E. Miesle; Thomas L. Johnson; Paul E. Dupont

[57] ABSTRACT

This invention relates to 3-aryl or heteroaryl-3-alkoxy, phenoxy-, alkylthio- or phenylthiophthalides useful as color formers, particularly in carbonless duplicating and thermal marking systems, which are prepared by the interaction of 2-(disubstituted amino)phenylcarbonylbenzoic acids with an acid chloride or an anhydride of an alkanoic acid in the first step and a further reaction of the product of the first step with an alcohol, a thioalcohol, a phenol or a thiophenol in a second step.

2 Claims, No Drawings

3-(ETHER AND THIOETHER)-3-(INDOLYL)-PHTHALIDES

CROSS REFERENCE TO RELATED APPLICATIONS

This application is a division of copending application Ser. No. 338,008, filed Jan. 8, 1982 now U.S. Pat. No. 4,535,172.

BACKGROUND OF THE INVENTION (a) Field of the Invention

This invention relates to novel compounds classified in the field of organic chemistry as 3-aryl- or 3-heteroaryl-3-alkoxy-, phenoxy-, alkylthio- or phenylthiophthalides useful as color precursors, particularly in the art of carbonless duplicating, for example, pressure-sensitive and thermal marking systems, to processes for preparing the phthalides and to pressure-sensitive and thermal marking systems containing the phthalides.

(b) Description of the Prior Art

Several classes of organic compounds of widely diverse structural types are known to be useful as colorless precursors for carbonless duplicating systems. Among the more important classes, there may be named phenothiazines, for example, benzoyl leuco methylene blue; phthalides, for example, Crystal Violet Lactone; fluorans, for example, 2'-anilino-6'-diethylaminofluoran and 2'-dibenzylamino-6'-diethylaminofluoran; arylsulfinate salts of Michler's Hydrol; and various other types of colorless precursors currently employed in commercially-accepted carbonless copy systems. Typical of the many such systems taught in the prior art are those described in U.S. Pat. Nos. 2,712,507, 2,800,457, 3,041,289 and 4,000,087, which issued July 5, 1955, July 23, 1957, June 26, 1962 and Dec. 28, 1976, respectively. Many of the color formers in the prior art suffer one or more disadvantages such as low tinctorial strength, poor light stability, low resistance to sublimation, low susceptibility to copiability of the color-developed form in standard office copying machines, for example, a xerographic type of copier, and low solubility in common organic solvents, the latter disadvantages thus requiring the use of specialized and expensive solvents in order to obtain microencapsulated solutions of sufficient concentration for use in pressure-sensitive copying systems.

The following items to date appear to constitute the most relevant prior art with regard to the instant invention.

Newman and McCleary in the Jounal of the American Chemical Society 63, 1537-1541 (1941) describe the preparation and physical characteristics of 3-phenyl-3-methoxyphthalide and an additional five phthalides bearing from one to three methyl substituents. These compounds were prepared by interacting in a first step 2-benzoylbenzoic acid or a methyl substituted derivative thereof with thionyl chloride with or without benzene to obtain the acid chloride. In a second step, the acid chloride was interacted with methanol in pyridine. No indication of utility for the compounds is given in the article.

Newman and Courduvelis in the Journal of Organic Chemistry 30, 1795-1800 (1965) describe the preparation of 3-phenyl-3-methoxyphthalide and methyl homologs thereof from the interaction of 2-benzoylbenzoic acid and methyl alcohol under acid catalyzed conditions. No indication of utility for the compounds is given in the article.

Newman and Courduvelis in the Journal of the American Chemical Society 88, 781-784 (1966) describe the preparation of 3-phenyl-3-methoxyphthalide from the interaction of 2-benzoylbenzoic acid with methylchlorocarbonate in the presence of 1,4-diazabicyclo[2,2,2]octane. No indication of utility for the compounds is given in the article.

Newman and Lala in Tetrahedron Letters 34, 3267-3269 (1967) describe the preparation of 3-phenyl-3-methoxyphthalide from the interaction of 3-phenyl-3-chlorophthalide with methyl alcohol in the presence of various organic bases. No indication of utility for the compounds is given in the article.

Bhatt and Kamath in the Journal of the Chemical Society (B) 1036-1044 (1968) describe the physical characteristics of 3-phenyl-3-methoxyphthalide and phthalides substituted in the 3-phenyl with cloro, bromo, methyl, nitro and cyano moieties and their preparation from the interaction of the appropriate 2-(substituted benzoyl)benzoic acids with thionyl chloride and subsequent interaction of the acid chloride with methanol in the presence of an organic base. No indication of utility for the compounds is given in the article.

SUMMARY OF THE INVENTION

The present invention in its composition of matter aspect, provides for novel 3-aryl- or heteroaryl-3-alkoxy-, alkylthio-, phenoxy-, or phenylthiophthalides which are useful as color formers in pressure-sensitive duplicating systems and in thermal marking systems. The compounds have enhanced solubility in common organic solvents and develop colored images of good to excellent tinctorial strength which have good light stability.

In one of its process aspects, the invention relates to a process for preparing a series of 3-aryl- or heteroaryl-3-alkoxy-, alkylthio-, phenoxy- or phenylthiophthalides which comprises interacting in a first step and appropriate aryl or heteroarylcarbonylbenzoic acid with thionyl chloride to obtain the corresponding acid chloride which is interacted in a second step with an excess of an alcohol, a thioalcohol, a phenol or a thiophenol in the presence of an organic base catalyst.

In a second of its process aspects, the invention relates to a process for preparing a series of 3-aryl- or heteroaryl-3-alkoxy-, alkylthio-, phenoxy- or phenylthiophthalides which comprises interacting an appropriate aryl or heteroarylcarbonylbenzoic acid with an anhydride of an alkanoic acid in a first step and interacting the product of the first step with an excess of an alcohol, a thioalcohol, a phenol or a thiophenol in the presence of an organic base catalyst.

The present invention provides in its articles of manufacture aspect, pressure-sensitive carbonless duplicating systems and thermal marking systems each containing at least one color-forming substance a 3-aryl- or heteroaryl-3-alkoxy-, alkylthio-, phenoxy- or thiophenoxyphthalide.

DETAILED DESCRIPTION INCLUSIVE OF THE PREFERRED EMBODIMENTS

More specifically, this invention in its composition of matter aspect, resides in the novel phthalides, which are particularly useful as colorless precursors in the art of carbonless duplicating and thermal marking and which are 3-(X-Y)-3-Z-4-$R^0$-5-R-6-$R^1$-7-$R^2$-phthalides of the formula

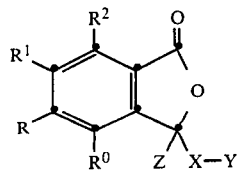

Formula I wherein $R^0$, R, $R^1$ and $R^2$ each represent hydrogen or halo or when $R^0$, $R^2$ and one of R and $R^1$ are each hydrogen the other of R and $R^1$ represents dialkylamino, dibenzylamino or N-alkylbenzylamino in which alkyl is non-tertiary $C_1$ to $C_4$ alkyl and benzyl is substituted in the benzene ring by one or two of halo or $C_1$ to $C_3$ alkyl; X represents oxygen or sulfur; Y represents a non-tertiary $C_1$ to $C_{16}$ or is selected from the group consisting of

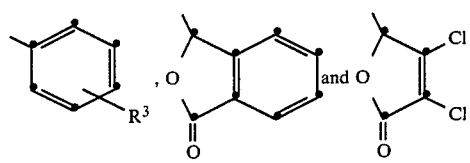

in which $R^3$ represents hydrogen, non-tertiary $C_1$ to $C_8$ alkyl, non-tertiary $C_1$ to $C_4$ alkoxy or halo; and Z is selected from the group consisting of

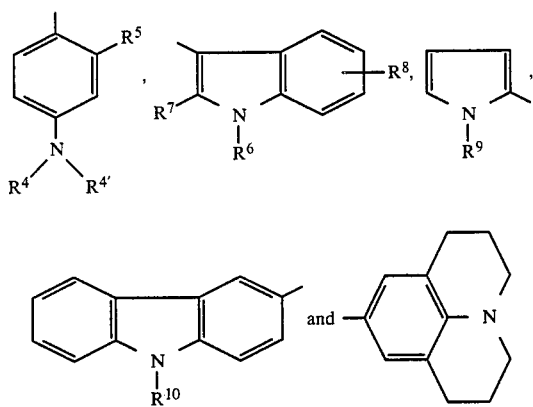

in which $R^4$ and $R^{4'}$ may be identical or different and each represents non-tertiary $C_1$ to $C_4$ alkyl, benzyl or benzyl substituted in the benzene ring by one or two of halo or $C_1$ to $C_3$ alkyl, $R^5$ represents hydrogen, $C_1$ to $C_3$ alkyl, non-tertiary $C_1$ to $C_4$ alkoxy, halo, dialkylamino, dibenzylamino or N-alkylbenzylamino in which alkyl is non-tertiary $C_1$ to $C_4$ alkyl and benzyl is substituted in the benzene ring by one or two of halo or $C_1$ to $C_3$ alkyl, $R^6$ represents hydrogen, non-tertiary $C_1$ to $C_{16}$ alkyl, benzyl or benzyl substituted in the benzene ring by one or two of halo or $C_1$ to $C_3$ alkyl, $R^7$, $R^9$ and $R^{10}$ represent hydrogen, $C_1$ to $C_3$ alkyl or phenyl, and $R^8$ represents one or two of hydrogen, $C_1$ to $C_3$ alkyl, $C_1$ to $C_3$ alkoxy, halo or nitro.

In a first particular embodiment in accordance with its composition of matter aspect, the invention sought to be patented resides in the novel 3-(X-Y)-3-(2-$R^5$-4-N-$R^4$-N-$R^{4'}$-aminophenyl)-4-$R^0$-5-R-6-$R^1$-7-$R^2$-phthalides of Formula I wherein z is 2-$R^5$-4-N-$R^4$-N-$R^{4'}$-aminophenyl according to the formula

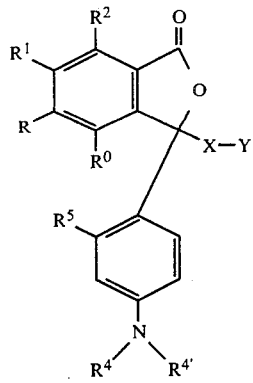

Formula II wherein $R^0$, R, $R^1$, $R^2$, $R^4$, $R^{4'}$, $R^5$, X and Y each have the same respective meanings given in Formula I.

In a second particular embodiment in accordance with the composition of matter aspect, the invention sought to be patented resides in novel 3-(X-Y)-3-(1-$R^6$-2-$R^7$-5/6-$R^8$-indol-3-yl)-4-$R^0$-5-R-6-$R^1$-7-$R^2$-phthalides of Formula I wherein Z is 1-$R^6$-2-$R^7$-5/6-$R^8$-indol-3-yl according to the formula

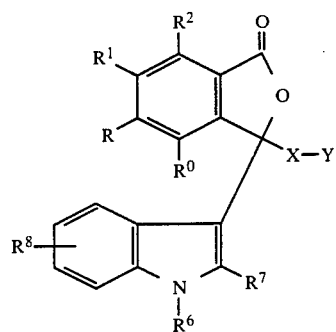

Formula III wherein $R^0$, R, $R^1$, $R^2$, $R^6$, $R^7$, $R^8$, X and Y each have the same meanings given in Formula I.

In a third particular embodiment in accordance with the composition of matter aspect, the invention sought to be patented resides in novel 3-(X-Y)-3-(1-$R^9$-pyrrol-2-yl)-4-$R^0$-5-R-6-$R^1$-7-$R^2$-phthalides of Formula I wherein Z is 1-$R^9$-pyrrol-2-yl according to the formula

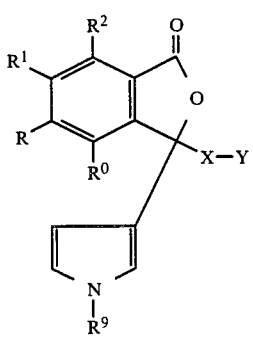

Formula IV wherein $R^0$, R, $R^1$, $R^2$, $R^9$, X and Y each have the same respective meanings given in Formula I.

In a fourth particular embodiment in accordance with the composition of matter aspect, the invention sought to be patented resides in novel 3-(X-Y)-3-(9-$R^{10}$-carbazol-3-yl)-4-$R^0$-5-R-6-$R^1$-7-$R^2$-phthalides of Formula I wherein Z is 9-$R^{10}$-carbazol-3-yl according to the formula

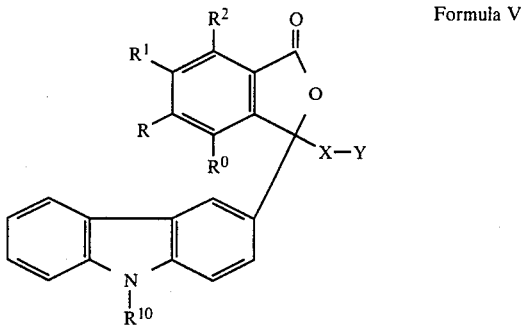

Formula V wherein $R^0$, R, $R^1$, $R^2$, $R^{10}$, X and Y each have the same respective meanings given in Formula I.

In one of its process aspects, the invention sought to be patented resides in the process for preparing a 3-(X-Y)-3-Z-4-$R^0$-5-R-6-$R^1$-7-$R^2$-phthalide according to Formula I which comprises interacting in the first step a 2-Z-carbonyl-3-$R^0$-4-R-5-$R^1$-6-$R^2$-benzoic acid having the formula

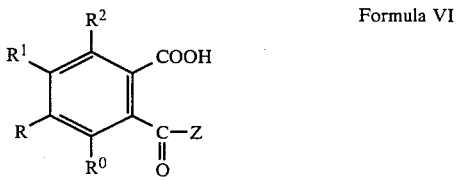

Formula VI with thionyl chloride to obtain the corresponding acid chloride and interacting in a second step, said acid chloride with a compound of the formula H-X-Y in the presence of an organic base catalyst wherein $R^0$, R, $R^1$, $R^2$, X, Y and Z each have the same respective meanings given in Formula I.

In a second of its process aspects, the invention sought to be patented resides in the process for preparing a 3-(X-Y)-3-Z-4-$R^0$-5-R-6-$R^1$-7-$R^2$-phthalide according to Formula I which comprises interacting in the first step a 2-Z-carbonyl-3-$R^0$-4-R-5-$R^1$-6-$R^2$-benzoic acid of Formula IV with an anhydride of an alkanoic acid having from two to five carbon atoms and in a second step, interacting the product of the first step with a compound of the formula H-X-Y in the presence of an organic base catalyst wherein $R^0$, R, $R^1$, $R^2$, X, Y and Z each having the same respective meanings given in Formula I.

In an article of manufacture aspect, the invention sought to be patented resides in a pressure-sensitive or thermal marking system comprising a support sheet coated with a layer containing as a color-forming substance a 3-(X-Y)-3-Z-4-$R^0$-5-R-6-$R^1$-7-$R^2$-phthalide according to Formula I wherein $R^0$, R, $R^1$, $R^2$, X, Y and Z each have the same respective meanings given in Formula I.

In a particular embodiment in accordance with its article of manufacture aspect, the invention sought to be patented resides in a pressure-sensitive transfer sheet, adapted for use with a receiving sheet having an electron-accepting layer, comprising a support sheet coated on one side with a layer of pressure-rupturable microcapsules; said microcapsules containing a liquid solution of a color-forming substance comprising at least one compound having Formula I.

Another embodiment in accordance with its article of manufacture aspect, resides in a heat responsive record material comprising a support sheet coated on one side with a layer containing a mixture comprising at least one color-forming compound having Formula I and an acidic developer arranged such that application of heat will produce a mark-forming reaction between the color-forming compound and the acidic developer.

As used herein the term "halo" includes chloro, fluoro, bromo and iodo. Chloro is the preferred halo substitute because of the relatively low cost and ease of preparation of the required chloro-substituted intermediates and because the other halogens offer no particular advantages over chloro. However, the other above-named halo substituents are also satisfactory.

The term "dialkylamino in which alkyl is non-tertiary $C_1$ to $C_4$ alkyl" denotes saturated, acyclic groups which may be straight or branched as exemplified by dimethylamino, diethylamino, ethylmethylamino, dipropylamino, dibutylamino, isobutylmethylamino and the like.

The term "N-alkylbenzylamino in which alkyl is non-tertiary $C_1$ to $C_4$ alkyl and benzyl may be substituted in the benzene ring by one or two of halo or $C_1$ to $C_3$ alkyl" denotes an amino moiety which is substituted with an acyclic group which may be straight or branched and one benzyl group as exemplified by N-methylbenzylamino, N-ethylbenzylamino, N-n-propylbenzylamino, N-sec-butylbenzylamino, N-ethyl(2,5-dimethylbenzyl)amino, N-ethyl(4-chlorobenzyl)amino and the like.

As used herein the terms "$C_1$ to $C_3$ alkyl", "non-tertiary $C_1$ to $C_4$ alkyl", "non-tertiary $C_1$ to $C_8$ alkyl" and "non-tertiary $C_1$ to $C_{16}$ alkyl" denote saturated monovalent straight or branched aliphatic hydrocarbon radicals including methyl, ethyl, propyl, isopropyl, butyl, isobutyl, amyl, 1-methylbutyl, 3-methylbutyl, hexyl, isohexyl, heptyl, isoheptyl, octyl, isooctyl, 2-ethylexyl, nonyl, 3-ethyl-heptyl, n-decyl, n-undecyl, n-dodecyl, n-tridecyl, n-ocotodecyl, 1,3,5-trimethylhexyl, 1,5-dimethyl-4-ethylhexyl, 5-methyl-2-butylhexyl, 2-propylnonyl, 2-butyloctyl, 2-pentanonyl, 1,2-dimethylhexadecyl and the like.

The terms "$C_1$ to $C_3$ alkoxy" and "non-tertiary $C_1$ to $C_4$ alkoxy" include saturated acyclic, straight or branched-chained groups such as methoxy, ethoxy, propoxy, isopropoxy, butoxy, sec-butoxy and isobutoxy.

The compounds of Formula I hereinabove are essentially colorless in the depicted form. When contacted with an acidic medium, for example, silica gel or one of the types ordinarily employed in pressure-sensitive carbonless duplicating systems such as silton clay or phenolic resins, the compounds of Formula I develop green, green-blue, blue, and yellow to orange-colored images. These developed images are very insensitive to light, are of good tinctorial strength, possess excellent xerographic copiability and enhanced solubility in common organic solvents. The compounds are thus highly suitable for use as colorless precursors, that is, color-forming substances in pressure-sensitive carbonless duplicating systems. The darker green and green-blue colors can be used alone as color formers to produce images which are readily copiable, whereas the yellow and orange colors can be used as toners in admixture with other color formers to produce images of a neutral shade which desirably are readily copiable by xerographic means.

The compounds of Formula I are more commonly adapted to use in admixture with one or more other color formers selected from the classes consisting of phthalides, for example, Crystal Violet Lactone; fluorans, for example, 2'-anilino-6'-diethylaminofluoran and 2'-dibenzylamino-6'-diethylaminofluoran; phenothiazines, for example, benzoyl leuco methylene blue; arylsulfinate salts of Michler's Hydrol; and various other types of colorless precursors currently employed in commercially-accepted carbonless copy systems.

The compounds of this invention may be incorporated in any of the commercially-accepted systems known in the carbonless duplicating art. A typical technique for such applications is as follows. Solutions containing one or more colorless compounds of Formula I optionally in admixture with other color formers, in suitable solvents are microencapsulated by well-known procedures, for example, as described in U.S. Pat. Nos. 3,649,649, 3,429,827 and 4,000,087. The microcapsules are coated on the reverse side of a sheet with the aid of a suitable binder and the coated transfer sheet is then assembled in a manifold with the microcapsule coated side in contact with a receiving sheet coated with an electron-accepting substance, for example, silton clay or a phenolic resin. Application of pressure to the manifold such as that exerted by a stylus, typewriter or other form of writing or printing causes the capsules on the reverse side to rupture. The solution of the color formers released from the ruptured microcapsules flows to the receiving sheet and on contact with the acidic medium thereon forms green to orange-colored images of good tinctorial strength. It is, of course, obvious that variants of this mode of application can be utilized. For example, the receiving sheet in a manifold can alternatively be coated with the subject compounds and the acidic developing agent can be contained in microcapsules applied to the reverse side of the top sheet in the manifold; or the receiving sheet can be coated with a mixture containing both the acidic developing agent and the microencapsulated color former.

It has also been found that when the compounds of Formula I are intimately mixed with an acidic developer of the type generally employed in thermal papers such as described in U.S. Pat. No. 3,539,375, that is, papers which produce a colored image when contacted with a heated stylus or heated type, for example, bisphenol A, heating of the mixture produces a colored image of varying shades from green to orange depending on the particular compound of the invention employed. The ability of the compounds of Formula I to form a deep color when heated in admixture with an acidic developer such as bisphenol A, makes them useful in thermal paper marking systems, either where an original or a duplicate copy is prepared by contacting the thermal paper with a heated stylus or heated type in any of the methods generally known in the art.

The best mode contemplated by the inventors of carrying out this invention will now be described so as to enable any person skilled in the art to which it pertains to make and use the same.

In accordance with one of the aforementioned process aspects of this invention the 3-(X-Y)-3-Z-4-$R^0$-5-R-6-$R^1$-7-$R^2$-phthalides of Formula I are obtained by reacting in a first step a 2-(Z)-carbonyl-3-$R^0$-4-R-5-$R^1$-6-$R^2$-benzoic acid of Formula VI with thionyl chloride in an appropriate inert organic liquid, for example, ethylene dichloride. This reaction is conveniently carried out at a temperature in the range of 0° to 60° C. for periods from approximately ten minutes to approximately three hours. The intermediate acid chloride or pseudo acid chloride is not isolated, but is utilized directly in the second step while still in solution. In a second step, an excess of an alcohol, a thioalcohol, a phenol, a thiophenol or a compound such as mucochloric acid or phthaldehyic acid is reacted with the acid chloride or pseudo acid chloride product from the first step in the presence of an organic base catalyst, for example, pyridine, tris(n-butyl)amine or 1,4-diazobicyclo[2,2,2]octane. The second reaction is conveniently carried out with the reaction medium obtained from the first step at a temperature in the range of 0° to 30° C. for approximately ten minutes to approximately seventy hours. The 3-(X-Y)-3-Z-4-$R^0$-5-R-6-$R^1$-7-$R^2$-phthalides of Formula I thus obtained can be isolated by pouring the reaction mixture into water or a dilute aqueous base, for example, ammonium hydroxide and the inert organic liquid layer containing the desired phthalide is separated from the water layer. The organic liquid layer may be washed with fresh water and/or treated with decolorizing charcoal and clarified. The phthalide is isolated from the organic liquid layer by evaporation of the organic liquid leaving the product as a residue. The isolated phthalide can be purified by conventional means such as trituration, recrystallization or reslurrying with a suitable organic liquid followed by filtration.

In accordance with another of the process aspects of this invention, the 3-(X-Y)-3-Z-4-$R^0$-5-R-6-$R^1$-7-$R^2$-phthalides of Formula I are obtained by interacting in a first step a 2-(Z)-carbonyl-3-$R^0$-4-R-5-$R^1$-6-$R^2$-benzoic acid of Formula VI with an anhydride of a alkanoic acid of two to five carbon atoms, for example, acetic anhydride or alternatively, a mixture of the anhydride and the alkanoic acid at a temperature in the range of 10° to 70° C. for approximately one-fourth to approximately two hours. The 3-substituted phthalide formed in the first step is not isolated. An excess of an alcohol, a thioalcohol, a phenol, a thiophenol or a compound such as mucochloric acid or phthaldehyic acid is reacted with the mono-substituted phthalide from the first step in the presence of an organic base catalyst, for example, pyridine, piperidine or the like. This reaction is conveniently carried out in the alkanoic acid anhydride or mixture of alkanoic acid and alkanoic acid anhydride remaining from the first step at a temperature in the range of 0° to 50° C. for periods of approximately one-half to approximately twenty hours. If necessary to effect a complete solution in the second step of the reaction a small amount of alkali, for example, potassium hydroxide may be added. The corresponding disubstituted phthalides thus obtained are isolated by slowly adding the reaction mixture to a mixture of water and a water soluble alkali, for example, ammonium hydroxide and extracting the product from the water layer into an organic liquid, for example, toluene. The organic liquid layer containing the product may be washed with fresh water and/or treated with decolorizing carbon and clarified. The phthalide is isolated by evaporating the organic solvent leaving the product as a residue. The isolated phthalide can be purified by conventional means, for example, trituration, recrystallization or reslurrying with a suitable organic liquid followed by filtration.

The 2-(Z)-carbonyl-3-$R^0$-4-R-5-$R^1$-6-$R^2$-benzoic acids of Formula VI required as starting materials in the preparation of the phthalides of Formula I constitute an old and well-known class of compounds readily obtained by conventional processes well-known in the art. These compounds and/or their preparation can be found in numerous patents, for example, U.S. Pat. Nos. 3,491,112, 3,509,174, 4,096,176, and 4,189,171.

The alcohols, thioalcohols, phenols or thiophenols which are required to obtain the 3-(X-Y)-3-Z-4-$R^0$-5-R-6-$R^1$-7-$R^2$-phthalides of Formula I belong to well-known classes of compounds and are generally commercially available or can be readily obtained by conventional means from readily available starting materials. The following compounds are exemplary of alcohols, thioalcohols, phenols and thiophenols useful in the processes of this invention: methanol, ethanol, 1-propanol, 2-propanol, 1-butanol, 2-butanol, 1-pentanol, 2-pentanol, 3-pentanol, 2-methyl-1-pentanol, 4-methyl-2-pentanol, 2-methyl-3-pentanol, 3-methyl-2-pentanol, 4-methyl-1-pentanol, 1-hexanol, 2-hexanol, 3-hexanol, 2-methyl-3-hexanol, 5-methyl-2-hexanol, 1-heptanol, 2-heptanol, 3-heptanol, 4-methyl-3-heptanol, 1-octanol, 2-octanol, 3-octanol, 1-nonanol, 2-nonanol, 1-decanol, 2-decanol, 4-decanol, 1-pentadecanol, 1-hexadecanol, 2-hexadecanol, ethanethiol, 1-propanethiol, 2-propanethiol, 2-methyl-1-propanethiol, 1-butanethiol, 2-methyl-1-butanethiol, 3-methyl-1-butanethiol, 1-pentanethiol, 1-heptanethiol, 1-nonanethiol, 1-octanethiol, 1-hexadecanethiol, phenol, 2-bromophenol, 3-bromophenol, 4-bromophenol, 2-chlorophenol, 3-chlorophenol, 4-chlorophenol, 2-fluorophenol, 3-fluorophenol, 4-fluorophenol, 4-iodophenol, 2-cresol, 3-cresol, 4-cresol, 2-ethylphenol, 3-ethylphenol, 4-ethylphenol, 2-propylphenol, 4-propylphenol, 2-isopropylphenol, 3-isopropylphenol, 4-isopropylphenol, 2-sec-butylphenol, 4-sec-butylphenol, 4-methoxyphenol, thiophenol, 4-chlorobenzenethiol, 4-bromobenzenethiol, 2-methoxybenzenethiol, 3-methoxybenzenethiol, 4-methoxybenzenethiol and the like.

The molecular structures of the compounds of this invention were assigned on the basis of the modes of synthesis and study of their infrared, nuclear magnetic resonance and mass spectra.

The following examples will further illustrate the invention without, however, limiting it thereto. All melting points are uncorrected.

EXAMPLE 1

With stirring and at 25° C., 5.2 g of 2-(4-dimethylaminophenyl)carbonyl-5-dimethylaminobenzoic acid was added to a mixture of 30.0 ml of ethylene dichloride and 1.2 ml of thionyl chloride. The resulting mixture was heated to and then maintained at approximately 50° C. for approximately ten minutes, and subsequently cooled to ambient temperature. To the resultant solution, there was added dropwise a solution of 20.0 ml of ethylene dichloride, 1.6 g of phenol and 2.0 ml of pyridine. After stirring the reaction solution for approximately eighteen hours at ambient temperature, the solution was poured slowly with stirring into a mixture of 200.0 ml of toluene and 250.0 ml of five percent aqueous ammonium hydroxide. The aqueous layer was separated from the toluene layer and the water layer was extracted with 100.0 ml of toluene. After separating the toluene layer from the water layer, the two toluene layers were combined and washed with 100.0 ml of five percent aqueous ammonium hydroxide. After separating the toluene layer from the aqueous ammonium hydroxide layer, the resulting toluene layer was filtered through diatomaceous earth. The filtered toluene layer was washed twice, once with 100.0 ml of fresh water and once with 100.0 ml of saturated aqueous sodium chloride solution. The toluene layer was then evaporated to obtain 5.3 g of a black solid. The solid was combined with 50.0 ml of acetone and the mixture was heated to the reflux temperature and then was cooled to ambient temperature. The separated material was collected by filtration and dried to obtain 1.85 g of a green solid. One gram of the green solid was heated in 90.0 ml of methyl alcohol, treated with decolorizing charcoal and the solution clarified by filtration. The filtered methyl alcohol solution was cooled to 0° C. The solid which formed was collected by filtration, washed with methyl alcohol chilled to 0° C. and dried to obtain 0.63 g of 3-phenoxy-3-(4-dimethylaminophenyl)-5-dimethylaminophthalide (Formula II: ($R^0$=R=$R^2$=$R^5$=H; $R^1$=N(CH$_3$)$_2$; $R^4$=$R^{4'}$=CH$_3$; X=O; Y=C$_6$H$_5$), a yellow solid which melted at 158° to 159° C. The infrared spectrum had a significant maximum at 1750 cm$^{-1}$ (C=O;s) and the nuclear magnetic resonance spectrum was concordant with the assigned structure. Analysis by mass spectrum showed m/e peaks at 388 (M$^+$) and 295 (M$^+$ −C$_6$H$_5$O). A toluene solution of the product spotted on an acidic clay-coated paper developed a blue-green-colored image.

EXAMPLE 2

A mixture of 6.3 g of 2-(4-dimethylaminophenyl)carbonyl-5-dimethylaminobenzoic acid and 150.0 ml of acetic anhydride was stirred for approximately fifteen minutes at ambient temperature. Slowly, 10.0 ml of piperidine and 10.0 ml of methyl alcohol were added to the mixture. Two grams of potassium hydroxide was added to complete the solution. The temperature rose to 55° C. with the addition of the potassium hydroxide. The resulting solution was allowed to stir overnight with gradual return to ambient temperature. Slowly, this solution was poured into a mixture of five percent aqueous ammonium hydroxide and toluene. After separation, the toluene layer was washed first with water and then with saturated aqueous sodium chloride solution. The resulting toluene layer was evaporated to dryness. The residue was slurried in 100.0 ml of isopropyl alcohol and the separated solid was collected by filtration, washed three times, each with 30.0 ml of isopropyl alcohol, and dried to obtain 4.0 g of 3-methoxy-3-(4-dimethylaminophenyl)-6-dimethylaminophthalide (Formula II: $R^0$=R=$R^2$=$R^5$=H; $R^1$=N(CH$_3$)$_2$; $R^4$=$R^{4'}$=Y=CH$_3$; X=O), a pale green solid which melted at 150° to 153° C. A significant infrared maximum appeared at 1765 cm$^{-1}$ (C=O;s). The nuclear magnetic resonance spectrum was in accord with the assigned structure. A toluene solution of the product spotted on an acidic clay-coated paper developed a green-colored image.

EXAMPLE 3

In a manner similar to that described in Example 1 above, 2.0 g of 2-(2-methyl-4-diethylaminophenyl)carbonylbenzoic acid, 0.77 g of thionyl chloride and 1.1 g of mucochloric acid were interacted in 20.0 ml of ethylene dichloride in the presence of 0.8 ml of pyridine to obtain 2.5 g of 3-[3,4-dichloro-2(5H)-furanon-5-yl]oxy- 3-(2-methyl-4-diethylaminophenyl)phthalide (Formula II: $R^0=R=R^1=R^2=H$; $R^4=R^{4'}=R^5=CH_3$; $X=O$; $Y=$3,4-dichloro-2-(5H)-furanon-5-yl), an orange-colored oil. A significant infrared maximum appeared at 1758 cm$^{-1}$ (C=O;s). A toluene solution of the product spotted on an acidic clay-coated paper developed a yellow-colored image.

EXAMPLE 4

Following a procedure similar to that described in Example 1 above, 4.5 g of 2-(4-dimethylaminophenyl)-carbonylbenzoic acid, 1.2 ml of thionyl chloride and 5.0 ml of methyl alcohol were interacted in 30.0 ml of ethylene dichloride in the presence of 1.3 ml of piperidine at ambient temperature for approximately ten minutes to obtain 4.0 g of 3-methoxy-3-(4-dimethylaminophenyl)phthalide (Formula II: $R^0=R=R^1=R^2=R^5=H$; $R^4=R^{4'}=R^5=Y=CH_3$; $X=O$), a pale peach-colored solid which melted at 112.5° to 114.5° C. A significant infrared maximum appeared at 1773 cm$^{-1}$ (C=O;s). The nulcear magnetic resonance spectrum was consistent with the assigned structure. Analysis by mass spectrum showed m/e peaks at 283 (M+) and 252 (M+ −OCH$_3$). A toluene solution of the product spotted on an acidic clay-coated paper developed a yellow-colored image.

EXAMPLE 5

Proceeding in a manner similar to that described in Example 1 above, 5.2 g of 2-(2-methyl-4-diethylaminophenyl)carbonylbenzoic acid, 1.2 ml of thionyl chloride and 5.0 ml of methyl alcohol were interacted in 30.0 ml of ethylene dichloride in the presence of 1.3 ml of pyridine to obtain 2.5 g of 3-methoxy-3-(2-methyl-4-diethylaminophenyl)phthalide (Formula II: $R^0=R=R^1=R^2=H$; $R^4=R^{4'}=C_2H_5$; $R^5=Y=CH_3$; $X=O$), a yellow-colored oil. A significant infrared maximum appeared at 1770 cm$^{-1}$ (C=O;s). The nuclear magnetic resonance spectrum was concordant with the assigned structure. Analysis by mass spectrum showed m/e peaks at 325 (M+) and 294 (M+ −OCH$_3$). A toluene solution of the product spotted on an acidic clay-coated paper developed a yellow-colored image.

EXAMPLE 6

Proceeding in a manner similar to that described in Example 1 above, 5.2 g of 2-(4-dimethylaminophenyl)-carbonyl-5-dimethylaminobenzoic acid, 1.2 ml of thionyl chloride and 1.8 g of thiophenol were interacted in 40.0 ml of ethylene dichloride in the presence of 2.0 ml of pyridine to obtain, after recrystallization of the product from isopropyl alcohol, 0.2 g of 3-phenylthio-3-(4-dimethylaminophenyl)-5-dimethylaminophthalide (Formula II: $R^0=R=R^2=R^5=H$; $R^1=N(CH_3)_2$; $R^4=R^{4'}=CH_3$; $X=S$; $Y=C_6H_5$), a white solid which melted at 185.5° to 187.5° C. The infrared spectrum had a significant maximum at 1770 cm$^{-1}$ (C=O;s). The nuclear magnetic resonance spectrum was consistent with the assigned structure. Analysis by mass spectrum showed a m/e peak at 403 (M+). A toluene solution of the product spotted on an acidic clay-coated paper developed a green-blue-colored image.

EXAMPLE 7

Following a procedure similar to that described in Example 1 above, 4.5 g of 2-(4-dimethylaminophenyl)-carbonylphthalide, 1.2 ml of thionyl chloride and 2.5 g of phthaldehydic acid were interacted in 50.0 ml of ethylene dichloride in the presence of 3.3 ml of pyridine to obtain 3.7 g of 3-(phthalid-3'-yl)oxy-3-(4-dimethylaminophenyl)phthalide (Formula II: $R^0=R=R^1=R^2=R^5=H$; $R^4=R^{4'}=CH_3$; $X=O$; $Y=$phthalid-3'-yl), a gray-white-colored solid which melted at 173° to 176° C. A significant infrared maximum appeared at 1785 cm$^{-1}$ (C=O;s). Analysis by mass spectrum showed m/e peaks at 401 (M+) and 252 (M+ −C$_8$H$_5$O$_3$). A toluene solution of the product spotted on an acidic clay-coated paper developed a yellow-colored image.

EXAMPLE 8

In a manner similar to that described in Example 1 above, 5.2 g of 2-(4-dimethylaminophenyl)carbonyl-5-dimethylaminobenzoic acid, 1.2 ml of thionyl chloride and 5.0 ml of methyl alcohol were interacted in 30.0 ml of ethylene dichloride in the presence of 1.3 ml of pyridine at ambient temperature overnight to obtain 4.5 g of 3-methoxy-3-(4-dimethylaminophenyl)-6-dimethylaminophthalide (Formula II: $R^0=R=R^2=R^5=H$; $R^1=N(CH_3)_2$; $R^4=R^{4'}=Y=CH_3$; $X=O$), a pale green-colored solid which melted over the range of 141° to 149° C. An infrared maximum appeared at 1770 cm$^{-1}$ (C=O;s). The nuclear magnetic resonance spectrum was consistent with the assigned structure. Analysis by mass spectrum showed m/e peaks at 326 (M+) and 295 (M+ −OCH$_3$). A toluene solution of the product spotted on an acidic clay-coated paper developed a green-colored image.

EXAMPLE 9

Proceeding in a manner similar to that described in Example 1 above, 5.1 g of 2-(1-ethyl-2-methylindol-3-yl)carbonylbenzoic acid, 1.2 ml of thionyl chloride and 5.0 ml of methyl alcohol were interacted in 30.0 ml of ethylene dichloride in the presence of 1.3 ml of pyridine to obtain 2.1 g of 3-methoxy-3-(1-ethyl-2-methylindol-3-yl)phthalide (Formula III: $R^0=R=R^1=R^2=R^8=H$; $R^6=C_2H_5$; $R^7=Y=CH_3$; $X=O$), a dark brown-colored oil. Significant infrared maxima appeared at 1770 (C=O;s) and 740 cm$^{-1}$ (C=O;s). Analysis by mass spectrum showed m/e peaks at 321 (M+) and 290 (M+ −OCH$_3$). A toluene solution of the product spotted on an acidic clay-coated paper developed a red-purple-colored image.

EXAMPLE 10

A. To a stirred mixture of 30.0 ml of acetic anhydride and 15.0 ml of glacial acetic acid there was added gradually 5.0 g of 2-(4-dimethylaminophenyl)carbonyl-5-dimethylaminobenzoic acid. The reaction mixture was heated slowly to approximately 47° C. and maintained at a temperature in the range of 45° to 50° C. for approximately thirty minutes. The resultant mixture was cooled to ambient temperature, stirred approximately forty-five minutes and then cooled to approximately 0° C. A solution of 15.0 ml of methyl alcohol and 19.4 ml of pyridine was added dropwise to the reaction mixture while maintaining a temperature of approximately 0° C. The resulting mixture was allowed to stir at ambient temperature for approximately two hours. After adding toluene to the reaction mixture, five percent aqueous ammonium hydroxide was added slowly until the resulting mixture was slightly alkaline. The toluene layer was separated from the alkaline water layer and toluene was removed under reduced pressure to obtain 4.67 g of 3-methoxy-3-(4-dimethylaminophenyl)-6-dimethylaminophthalide (Formula II: $R^0=R=R^2=R^5=H$; $R^1=N(CH_3)_2$; $R^4=R^{4'}=Y=CH_3$; $X=O$), a pale green-colored solid which melted at 140° to 147° C. A significant infrared maximum appeared at 1760 cm$^{-1}$ (C=O;s). The nuclear magnetic resonance spectrum was consistent with the assigned structure. A toluene solution of the product spotted on an acid-clay coated paper developed a turquoise-colored image.

B. Proceeding in a manner similar to that described in part A directly above except substituting 26.9 g of 1,4-diazobicyclo[2,2,2]octane for the 19.4 ml of pyridine there was obtained 4.45 g of 3-methoxy-3-(4-dimethylaminophenyl)-6-dimethylaminophthalide (Formula II: $R^0=R=R^2=R^5=H$; $R^1=N(CH_3)_2$; $R^4=R^{4'}=Y=CH_3$; $X=O$), a pale green-colored solid which melted at 140° to 147° C. The analysis of this product was identical to the product obtained in part A above.

C. Proceeding in a manner similar to that described in part A directly above except substituting 44.5 g of tri-n-butylamine for 19.4 ml of pyridine there was obtained 2.63 g of 3-methoxy-3-(4-dimethylaminophenyl)-6-dimethylaminophthalide (Formula II: $R^0=R=R^2=R^5=H$; $R^1=N(CH_3)_2$; $R^4=R^{4'}=Y=CH_3$; $X=O$), a pale green-colored solid which melted at 140° to 147° C. The analysis of this product was identical to part A above.

The following table (Table A) lists 3-(X-Y)-3-Z-4-$R^0$-5-R-6-$R^1$-7-$R^2$-phthalides prepared from the interaction of a 2-Z-carbonyl-3-$R^0$-4-R-5-$R^1$-6-$R^2$-benzoic acid of Formula VI with the appropriate alcohol, thioalcohol, phenol or thiophenol in the presence of an alkaline amine catalyst in a manner similar to that described in Examples 1 and 3 through 9 above. The starting benzoic acids listed in the second column were interacted with the alcohols shown in the sixth column in the presence of the catalyst indicated in the fifth column. The substituted phthalide product obtained is listed in the seventh column and the product's appearance and melting point is indicated in the eighth and ninth columns, respectively. A significant infrared maximum is shown in the tenth column and the results of the nuclear magnetic spectral analysis is shown in the eleventh column. The substituted phthalides were tested as carbonless duplicating color precursors by dissolving the product in toluene and streaking the toluene solution on an acidic clay-coated paper sheet. The colors of the images which developed in this streaking test are indicated in the twelth column of the table. Table A has been divided in two parts, Part I contains Columns 1 through 6 and Part II contains Columns 7 through 12.

TABLE A

| Example No. | Starting Benzoic Acid | Thionyl Chloride | Ethylene Dichloride | Catalyst | Alcohol | Phthalide Product | Product Color | Melting Point °C. | IR cm−1 | NMR | Developed Color on Clay-Coated Paper |
|---|---|---|---|---|---|---|---|---|---|---|---|
| 11 | 5.0 g 2-(4-Dimethylaminophenyl)-carbonyl-5-dimethylamino-benzoic Acid | 1.2 ml | 50.0 ml | 1.9 g Pyridine | 20.0 ml Isopropyl Alcohol | 2.01 g 3-Isopropoxy-3-(4-dimethylaminophenyl)-6-dimethylamino-phthalide | Pale Green | 111.8-114.7 | 1755 (C=O;s) | Consistent | Turquoise |
| 12 | 3.0 g 2-(9-Ethylcarbazol-3-yl)-carbonylbenzoic Acid | 0.61 ml | 40.0 ml | 1.0 g Pyridine | 15.0 ml Methyl Alcohol | 0.56 g 3-Methoxy-3-(9-ethyl-carbazol-3-yl)-phthalide | Pale Blue-Tan | | 1765 (C=O;s) | Consistent | Light Gray |
| 13 | 1.0 g 2-(1-Methylpyrrol-3-yl)-carbonylbenzoic Acid | 0.32 ml | 10.0 ml | 0.52 g Pyridine | 5.0 ml Methyl Alcohol | 0.46 g 3-Methoxy-3-(1-methylpyrrol-3-yl)-phthalide | Rust | | 1760 (C=O;s) | Consistent | Light Gray |
| 14 | 3.0 g 2-(1-n-Butyl-2-methylindol-3-yl)carbonylbenzoic Acid | 0.61 ml | 15.0 ml | 1.0 g Pyridine | 15.0 ml Methyl Alcohol | 4.58 g 3-Methoxy-3-(1-n-butyl-2-methylindol-3-yl)phthalide | Pale Green | | 1780 (C=O;s) | Consistent | Light Pink |
| 15 | 3.0 g 2-(1-Ethyl-2-methylindol-3-yl)-3,4,5-tetrachloro-benzoic Acid | 0.49 ml | 30.0 ml | 0.8 g Pyridine | 15.0 ml Methyl Alcohol | 0.08 g 3-Methoxy-3-(1-ethyl-2-methylindol-3-yl)-phthalide | Purple | | 1776 (C=O;s) | | Light Pink |
| 16 | 5.0 g 2-(4-Dimethylaminophenyl)-carbonylbenzoic Acid | 1.3 ml | 20.0 ml | 2.1 g Pyridine | 1.6 ml n-Butyl Alcohol | 4.2 g 3-n-Butoxy-3-(4-dimethylaminophenyl)-phthalide | Pale Purple | 48-50 | 1770 (C=O;s) | Consistent | Yellow |
| 17 | 3.0 g 2-(2-Ethoxy-4-diethylamino-phenyl)carbonylbenzoic Acid | 0.61 ml | 30.0 ml | 1.0 g Pyridine | 15.0 ml Methyl Alcohol | 2.4 g 3-Methoxy-3-(2-ethyl-4-diethylaminophenyl)-phthalide | Orange | 112-114 | 1765 (C=O;s) | Consistent | Yellow |
| 18 | 5.0 g 2-(4-Dimethylaminophenyl)-carbonyl-5-dimethylamino-benzoic Acid | 1.2 ml | 40.0 ml | 1.9 g Pyridine | 20.0 ml Methyl Alcohol | 3.0 g 3-Methoxy-3-(4-dimethylaminophenyl)-6-dimethylaminophthalide | Green | 140-147 | 1760 (C=O;s) | Consistent | Turquoise |
| 19 | 5.0 g 2-(4-Dimethylaminophenyl)-carbonylbenzoic Acid | 1.3 ml | 20.0 ml | 2.1 g Pyridine | 1.8 ml 3-Methyl-2-buten-1-ol | 3.6 g 3-(3-Methyl-2-buten-1-oxy)-3-(4-dimethyl-aminophenyl)phthalide | Pale Purple | 90-92 | 1762 (C=O;s) | Consistent | Orange |
| 20 | 5.0 g 2-(4-Dimethylaminophenyl)-carbonylbenzoic Acid | 1.3 ml | 20.0 ml | 2.1 g Pyridine | 2.8 ml n-Octyl Alcohol | 5.1 g 3-n-Octoxy-3-(4-dimethylaminophenyl)-phthalide | Red | Oil | 1775 (C=O;s) | Consistent | Yellow |
| 21 | 5.0 g 2-(4-Dimethylaminophenyl)-carbonylbenzoic Acid | 1.3 ml | 20.0 ml | 2.1 g Pyridine | 20.0 ml n-Butyl Alcohol | 3.2 g 3-n-Butoxy-3-(4-dimethylaminophenyl)-phthalide | Brown | Oil | 1775 (C=O;s) | Consistent | Yellow |
| 22 | 5.0 g 2-(4-Dimethylaminophenyl)-carbonylbenzoic Acid | 1.3 ml | 20.0 ml | 2.1 g Pyridine | 20.0 ml Isopropyl Alcohol | 4.2 g 3-Isopropoxy-3-(4-dimethylaminophenyl)-phthalide | Pale Blue | 133.5-136 | 1760 (C=O;s) | Consistent | Yellow |
| 23 | 5.0 g 2-(2-Methylindol-3-yl)-carbonylbenzoic Acid | 1.3 ml | 20.0 ml | 2.1 g Pyridine | 20.0 ml Methyl Alcohol | 3.4 g 3-Methoxy-3-(2-methylindol-3-yl)phthalides | Tan | 126-128 | 1765 (C=O;s) | Consistent | Pink |
| 24 | 5.0 g 2-(4-Dimethylaminophenyl)-carbonylbenzoic Acid | 1.3 ml | 40.0 ml | 2.1 g Pyridine | 4.4 g n-Hexadecyl Alcohol | | | | | | |

It is contemplated that by following the procedures described in the foregoing examples but employing the appropriate 2-Z-carbonyl-3-$R^0$-4-R-5-$R^1$-6-$R^2$-benzoic acid of Formula VI with the appropriate alcohol, thioalcohol, phenol or thiophenol, there will be obtained 3-(X-Y)-3-Z-4-$R^0$-5-R-6-$R^1$-7-$R^2$-phthalides of Formula I, Examples 25–50, presented in Table B hereinbelow. Table B has been divided into two parts, Part I contains Columns 1 through 6 which contain substituents $R^0$, R, $R^1$, $R^2$ and X and Part II contains Columns 7 and 8 which contain substituents Y and Z.

Phthalides of Formula I

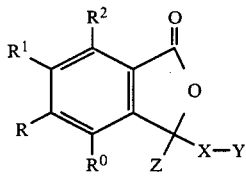

was heated at approximately 50° C. for about one hour.

B. Two solutions, the first containing the product and the isopropylbiphenyl, and the second containing the carboxymethylcellulose and the water were mixed and emulsified using a variable speed one-half horsepower Eppenbach Homo-Mixer (Gifford-Wood Co., Hudson, N.Y.) for approximately five minutes at an applied voltage of 50 volts until the particle size of the suspended emulsion was approximately 2 microns at approximately 50° C. While maintaining the rapid agitation, the third solution containing the gelatin and water was added and the pH adjusted to 6.5 with the addition of 5 percent aqueous sodium hydroxide. Slowly, 660.0 ml of distilled water at approximately 50° C. was added and the pH adjusted to 4.5 by the addition of 10 percent aqueous acetic acid. After five minutes of rapid agitation, the mixture was cooled to approximately 15° C. by means of an external ice-water bath and 10.0 ml of a twenty-five percent glutaraldehyde solution was added dropwise and agitation continued for 15 minutes. At this time, the Ep-

TABLE B

Phthalides of Formula I

| Example | $R^0$ | R | $R^1$ | $R^2$ | X | Y | Z |
|---|---|---|---|---|---|---|---|
| 25 | Cl | Cl | Cl | Cl | O | n-$C_5H_{11}$ | 2-n-Butoxy-4-diethylaminophenyl |
| 26 | H | H | H | H | O | sec-$C_5H_{11}$ | 2-Chloro-4-dimethylaminophenyl |
| 27 | Br | Br | Br | Br | O | 2-$CH_3C_5H_{10}$ | 2,4-Bis(dibenzylamino)phenyl |
| 28 | H | H | H | H | O | 3-$CH_3C_5H_{10}$ | 4-(Di-sec-butyl)aminophenyl |
| 29 | H | H | H | H | O | 3-$CH_3C_5H_{10}$ | 4-N—Ethyl-N—benzylaminophenyl |
| 30 | H | H | N($CH_3$)$_2$ | H | O | n-$C_6H_{13}$ | 2-Methoxy-4-di-n-butylaminophenyl |
| 31 | Cl | Cl | Cl | Cl | O | n-$C_8H_{17}$ | 9-Julolidinyl |
| 32 | H | N($C_2H_5$)$_2$ | H | H | O | n-$C_{10}H_{21}$ | 1-Octyl-2-methylindol-3-yl |
| 33 | H | H | H | H | O | n-$C_{16}H_{33}$ | 2-Ethylindol-3-yl |
| 34 | H | H | N(n-$C_3H_7$)$_2$ | H | S | n-$C_3H_7$ | 1-Hexadecyl-2-ethylindol-3-yl |
| 35 | Br | Br | Br | Br | S | n-$C_4H_9$ | 1-Benzyl-2-methylindol-3-yl |
| 36 | H | H | H | H | S | 2-$CH_3C_4H_8$ | 2-Bromo-4-N—ethyl-N—(4-chlorobenzyl)aminophenyl |
| 37 | H | H | N($CH_2C_6H_5$)$_2$ | H | S | n-$C_7H_{15}$ | 1-(4-Methylbenzyl)indol-3-yl |
| 38 | H | H | N(n-$C_4H_9$)$_2$ | H | S | n-$C_9H_{19}$ | 1-Dodecyl-2-methylindol-3-yl |
| 39 | H | NH$CH_2C_6H_5$ | H | H | S | n-$C_{16}H_{33}$ | 2-Iodo-4-di-(4-methylbenzyl)-aminophenyl |
| 40 | H | H | N(4-Cl$C_6H_5CH_2$)$_2$ | H | O | 2-Br$C_6H_4$ | 2-n-Propyl-4-diethylaminophenyl |
| 41 | H | N(sec-$C_4H_9$)$_2$ | H | H | O | 3-Cl$C_6H_4$ | 2,4-Bis(di-n-butylamino)phenyl |
| 42 | H | H | N(iso-$C_3H_7$)$_2$ | H | O | 4-F$C_6H_4$ | 2-n-Propylindol-3-yl |
| 43 | F | F | F | F | O | 4-$CH_3OC_6H_4$ | 2-Phenylindol-3-yl |
| 44 | H | H | H | H | O | 4-n-$C_6H_{13}OC_6H_4$ | 1-Phenylpyrrol-2-yl |
| 45 | H | H | N($CH_3$)$_2$ | H | O | 3-$C_2H_5C_6H_4$ | 9-Methylcarbazol-1-yl |
| 46 | H | H | H | H | S | 2-$CH_3OC_6H_4$ | 9-Phenylcarbazol-1-yl |
| 47 | Cl | Cl | Cl | Cl | S | 3-$CH_3OC_6H_4$ | 1-n-Propylpyrrol-2-yl |
| 48 | H | N(n-$C_3H_7$)$_2$ | H | H | S | $C_6H_5$ | 9-Julolidinyl |
| 49 | H | H | N—$C_2H_5$—N—$CH_2C_6H_5$ | H | S | 4-Br$C_6H_4$ | 1-n-Hexyl-2-ethylindol-3-yl |
| 50 | H | H | H | H | S | 4-Cl$C_6H_4$ | 1-4-(Chlorobenzyl)-2-methylindol-3-yl |

EXAMPLE 51

The use of the compounds of Formula I described in Examples 1 through 50, as color-forming components in pressure-sensitive microencapsulated copying systems is illustrated with reference to the product of Example 2.

A. A mixture of 60.0 g of isopropylbiphenyl and 1.46 g of 3-methoxy-3-(4-dimethylaminophenyl)-6-dimethylaminophthalide, prepared as described above in Example 2, was heated to 100° C. until a clear solution was formed and then cooled to approximately 50° C. A second solution of 5.0 g of carboxymethylcellulose dissolved in 200.0 ml of distilled water was prepared. A third solution containing 15.0 ml of 275 Bloom gelatin dissolved in 120.0 ml of distilled water penbach Homo-Mixer was replaced with a conventional blade type laboratory agitator and the suspension was stirred overnight. The suspension was adjusted to 1120.0 g with the addition of distilled water.

C. The stock microcapsule suspension prepared in part B above was coated on paper sheets to a thickness of approximately 0.0015 inch and the coated paper air dried. The paper thus coated with the microencapsulated colorless precursor was assembled as the top sheet in a manifold system by positioning the coated side in contact with the coated side of a commercially-available receiving sheet coated with a color developer of the electron-accepting type. More specifically, papers coated with a phenolic resin and with an acidic clay were employed in this test. An image was then drawn with a stylus on the top sheet bearing the microencapsulated colorless precursor on its reverse side causing the affected microcapsules to rupture thus allowing the solution of the colorless precursor held by said microcapsules to flow into contact with the color-developing substance on the receiving sheet whereupon a pale green-colored image slowly formed on the resin-coated sheet and a pale blue-green-colored image on the clay-coated sheet.

EXAMPLE 52

The utility of the compounds of Formula I whose preparations are described in the foregoing examples as color-forming components in thermal marking systems is illustrated by the incorporation and testing of the compound of Example 1, 3-phenoxy-3-(4-dimethylaminophenyl)-6-dimethylaminophthalide, in a thermal-sensitive marking paper. The test paper was prepared by a procedure similar to that described in U.S. Pat. No. 3,539,375.

A. A mixture of 1.0 g of 3-phenoxy-3-(4-dimethylaminophenyl)-6-dimethylaminophthalide, 4.3 g of a ten percent aqueous solution of polyvinyl chloride (approximately 99 percent hydrolyzed), 1.9 g of water and 15.8 g of 1/16 inch diameter zirconium grinding beads were charged into a container which was placed in a mechanical shaker. Shaking was effected for one hour. The zirconium beads were then removed by straining the mixture through a No. 40 sieve.

B. Similarly, a mixture of 9.8 g of 4,4'-isopropylidine diphenol (Bisphenol A), 42.0 g of a ten percent aqueous polyvinyl alcohol solution (approximately 99 percent hydrolyzed), 18.2 g of water and 221.2 g of 1/16 inch diameter zirconium grinding beads was charged into a container which was placed in a mechanical shaker. After shaking was effected for one hour, the zirconium beads were removed by straining through a No. 40 sieve.

C. A coating composition was prepared by mixing 2.1 g of the slurry from part A and 47.9 g of the slurry from part B. The mixture was then uniformly coated onto sheets of paper at a thickness of approximately 0.0015 inch and the coated sheets air dried. The coated paper was tested by tracing a design on the coated side of the paper placed on a smooth flat surface with a stylus heated to approximately 150° C. A green-colored image corresponding to the traced design promptly developed.

When evaluated in thermal marking paper prepared and tested as described above, the product of Example 6, 3-phenylthio-3-(4-dimethylaminophenyl)-6-dimethylaminophthalide, produced a green-colored image at approximately 175° C.; and the product of Example 8, 3-methoxy-3-(4-dimethylaminophenyl)-6-dimethylaminophthalide, produced a green-colored image at approximately 150° C.

What is claimed is:

1. A 3-(X-Y)-3-Z-4-R$^0$-5-R-6-R$^1$-7-R$^2$-phthalide of the formula

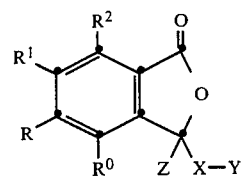

Formula I wherein:
R$^0$ R, R$^1$ and R$^2$ each represent hydrogen or halo or when R$^0$, R$^2$ and one of R and R$^1$ are each hydrogen, the other of R and R$^1$ represents dialkylamino, dibenzylamino or N-alkylbenzylamino in which alkyl is non-tertiary C$_1$ to C$_4$ alkyl and benzyl is substituted in the benzene ring by one or two of halo or C$_1$ to C$_3$ alkyl;

X represents oxygen or sulfur;

Y represents a non-tertiary C$_1$ to C$_{16}$ alkyl or is selected from the group consisting of

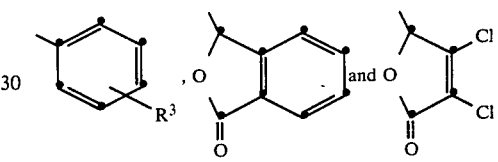

in which
R$^3$ represents hydrogen, non-tertiary C$_1$ to C$_8$ alkyl, non-tertiary C$_1$ to C$_4$ alkoxy or halo;

Z is

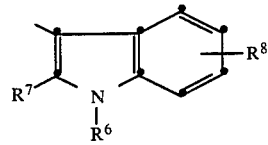

in which
R$^6$ represents hydrogen, non-tertiary C$_1$ to C$_{16}$ alkyl, benzyl or benzyl substituted in the benzene ring by one or two of halo or C$_1$ to C$_3$ alkyl;
R$^7$ represents hydrogen, C$_1$ to C$_3$ alkyl or phenyl; and
R$^8$ represents one or two of hydrogen, C$_1$ to C$_3$ alkyl, C$_1$ to C$_3$ alkoxy, halo or nitro.

2. 3-Methoxy-3-(1-ethyl-2-methylindol-3-yl)phthalide according to claim 1.

* * * * *